United States Patent
Netzhammer

(10) Patent No.: US 8,997,765 B2
(45) Date of Patent: Apr. 7, 2015

(54) DEVICE FOR TREATING SMALL PARTS

(75) Inventor: Eric Netzhammer, Bottmingen (CH)

(73) Assignee: Eric Netzhammer, Bottmingen (CH)

( * ) Notice: Subject to any disclaimer, the term of this patent is extended or adjusted under 35 U.S.C. 154(b) by 0 days.

(21) Appl. No.: 13/123,141

(22) PCT Filed: Oct. 7, 2008

(86) PCT No.: PCT/EP2008/063390
§ 371 (c)(1),
(2), (4) Date: Jun. 21, 2011

(87) PCT Pub. No.: WO2010/040383
PCT Pub. Date: Apr. 15, 2010

(65) Prior Publication Data
US 2011/0240069 A1  Oct. 6, 2011

(51) Int. Cl.
*A61L 2/06* (2006.01)
*A61L 2/07* (2006.01)
*A61L 2/26* (2006.01)
*B08B 3/04* (2006.01)

(52) U.S. Cl.
CPC ... *A61L 2/07* (2013.01); *A61L 2/26* (2013.01); *B08B 3/045* (2013.01); *B08B 3/047* (2013.01)

(58) Field of Classification Search
CPC ........................................ A61L 2/00
USPC ........................................ 134/200
See application file for complete search history.

(56) References Cited

U.S. PATENT DOCUMENTS

| | | | |
|---|---|---|---|
| 2,795,404 A | 3/1954 | Cornell, Jr. | |
| 3,552,405 A * | 1/1971 | Apel | 134/65 |
| 4,059,919 A * | 11/1977 | Green | 47/1.1 |
| 5,022,419 A * | 6/1991 | Thompson et al. | 134/102.1 |
| 6,827,302 B2 * | 12/2004 | Hohnen et al. | 241/46.13 |
| 2003/0019961 A1 | 1/2003 | Hohnen et al. | |
| 2006/0090367 A1 | 5/2006 | Bringewatt et al. | |

FOREIGN PATENT DOCUMENTS

| | | | | |
|---|---|---|---|---|
| DE | 10235374 A1 | 2/2004 | | |
| JP | 2000-157777 A * | 8/1999 | | D06F 21/10 |
| JP | 2002-210424 * | 7/2002 | | B08B 3/12 |
| JP | 2008-104904 * | 5/2008 | | B08B 3/02 |
| WO | 03009942 A1 | 2/2003 | | |
| WO | 2004029351 A2 | 4/2004 | | |

* cited by examiner

*Primary Examiner* — Michael Barr
*Assistant Examiner* — Jason Riggleman
(74) *Attorney, Agent, or Firm* — Fitch, Even, Tabin & Flannery LLP

(57) ABSTRACT

A device for gently cleaning, sterilizing, and drying large volumes of small parts, having a stationary, preferably spherical treatment container optionally having a cooling device and having a rotating inner basket disposed in the interior thereof. The inner basket is preferably sealed off from the treatment container and driven by a stepper motor or servo motor.

8 Claims, 2 Drawing Sheets

DEVICE FOR TREATING SMALL PARTS

CROSS-REFERENCE TO RELATED APPLICATIONS

This application is the National Stage filing under 35 U.S.C. 371 of International Application No. PCT/EP2006/063390, filed Oct. 7, 2008, which is incorporated herein, in its entirety, by reference.

BACKGROUND OF THE INVENTION

The invention relates to a device for gently cleaning, sterilizing and drying large volumes of small parts. These parts can be, for example, parts of syringes or ampoules, thus parts which are primarily used in the medical field.

For carrying out these processes, different machines and methods are known which, however, have some disadvantages whether in the area of the methods or in the area of the machine design.

A known system consists of a mobile treatment container having a rotating inner basket into which the parts are placed. The basket is coarsely perforated similar to a washing machine for clothes. After the treatment is completed, the parts are transported in said treatment container to the consumer and handed over to the same. The disadvantage of this system is that the coarse perforation generates a poor fluid bed and therefore, no uniform treatment takes place due to the media flow flowing in an uncontrolled manner through the parts to be treated. Particularly disadvantageous is that it is possible that the media flow can even flow past the outside of the treatment basket and consequently the parts do not come into contact with the media at all and therefore are not treated.

A further known system consists of a rotating mobile treatment container having a screen plate or a fine-meshed screen, usually sintered, as support for the small parts. The media necessary for carrying out the treatment flow through said screen plate and generate a so-called fluid bed which effects the treatment. Upon completion of the treatment, as in the case of the aforementioned system, the parts are transported in said container to the consumer and handed over to the same. The disadvantage of this method is that the treatment container has to be rotated which is very complicated with respect to process engineering. All connections have to be designed to be rotatable and, in addition, the decoupling has to be carried out under sterile conditions so that the coupling to the consumer can be carried out again under sterile conditions. A further serious disadvantage is that the parts have to be "consumed" immediately, i.e. have to be handed over to the consumer immediately after the treatment. A temporary storage under sterile conditions is possible; however, if large volumes are involved and a temporary storage of the parts is necessary, a plurality of treatment containers has to be available. This results in high investment costs because such treatment containers are complex and have to be highly instrumented in order to cover the treatment requirements.

Also known are treatment containers which are not used as transport containers, but are permanently installed. After the treatment, the parts are placed mostly in movable transport containers and are stored therein under sterile conditions until they can be delivered to the consumer.

Such systems too have the disadvantage that the treatment container has to be rotated which is very complicated in terms of process engineering because all connections have to be designed to be rotatable.

SUMMARY OF THE INVENTION

The invention is based on the object to eliminate the existing problems for the described processes.

According to the invention, this is achieved by a stationary treatment container having an inner basket arranged in the interior of said treatment container.

The invention is based on the following considerations which in known systems have not been considered or only insufficiently and which are therefore novel in their entirety. For the treatment of small parts, basically, some important principles are to be considered:

- The parts require a gentle treatment. This can be achieved by carefully rotating the surrounding container.
- Remaining water and condensate have to be drained. The small parts often contain cavities which have to be drained for a uniform treatment quality. This can also be achieved by carefully rotating the surrounding container.
- The media steam, water, air have to be guided correctly so that they actually come into contact with the parts to be treated and that it is ensured that all parts receive the same treatment quality.
- Since in the installation space in the installations is in most cases very limited, it is necessary to develop designs with a treatment volume as high as possible and small outer dimensions.
- The positioning accuracy of rotating machines is important so that the small treated parts undergo the correct material flow. For example, it is important that no small parts are treated multiple times which can happen if a part has not been unloaded correctly.

BRIEF DESCRIPTION OF THE FIGURES

Hereinafter, preferred exemplary embodiments of the invention are described by means of the enclosed drawings. In the figures.

DETAILED DESCRIPTION OF THE INVENTION

A device to gently clean, sterilize, and dry large volumes of small parts in a fluid bed is provided. In an aspect of the invention, device for gently cleaning, sterilizing and drying large volumes of small parts has a stationary treatment container, preferably a spherical treatment container, optionally having a cooling device and having a rotating inner basket disposed in the interior of the treatment container.

In an aspect of the invention, the device is for gently cleaning, sterilizing and drying large volumes of small parts, includes a stationary treatment container having an inner basket. The inner basket is arranged in the interior of the treatment container and is rotatable about a horizontal axis. The inner basket has a screen bottom.

In an aspect of the invention, the device for gently cleaning, sterilizing and drying large volumes of small parts includes a movable seal between the treatment container and the inner basket.

In an aspect of the invention, the device for gently cleaning, sterilizing and drying large volumes of small parts has a treatment container that has a spherical shape.

In an aspect of the invention, the device for gently cleaning, sterilizing and drying large volumes of small parts has the rotatable inner basket rotated with a stepper motor or servo motor arranged outside of the treatment container. In an aspect of the invention, the device for gently cleaning, sterilizing and drying large volumes of small parts has the inner basket provided with a screen flap that is arranged opposite to the screen bottom.

In an aspect of the invention, the device for gently cleaning, sterilizing and drying large volumes of small parts includes a cooling unit arranged on the treatment container.

Figure 1:
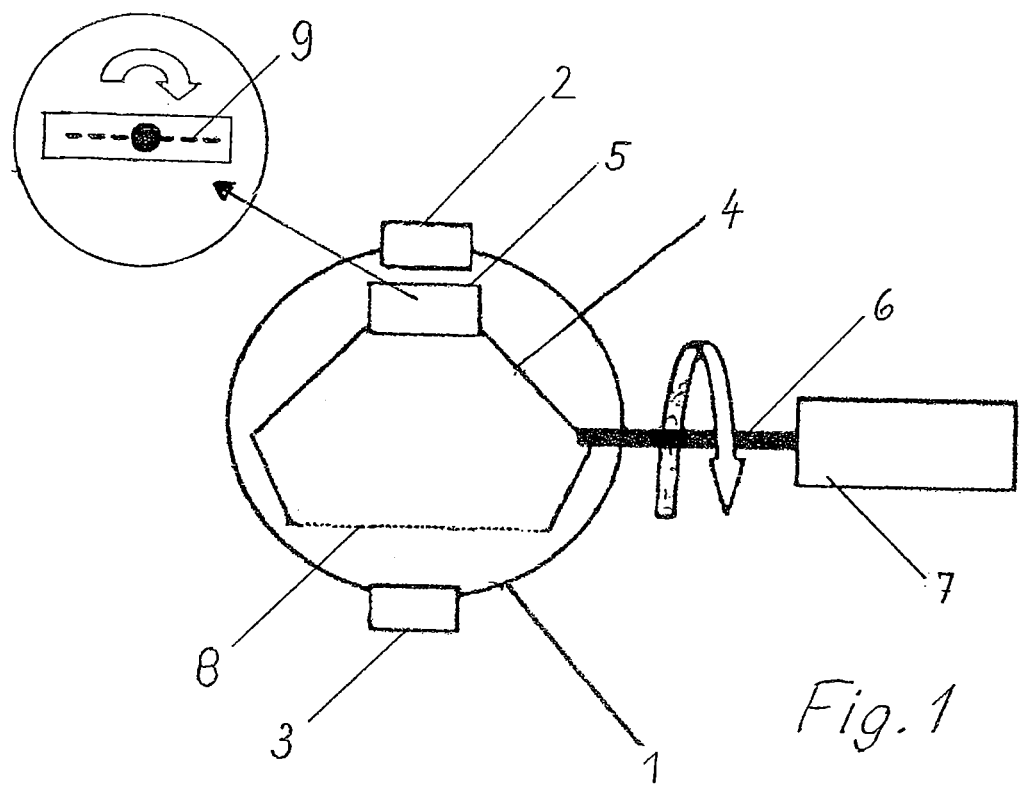
FIG. 1 shows a schematic illustration of the device according to the invention.

The spherical treatment container 1 shown in FIG. 1 is stationary, i.e. it is permanently installed and has no function as transport container. In this manner, a simple installation and a simple construction of the treatment container are possible. The treatment container has an opening 2 on its upper side through which the loading takes place and an unloading opening 3 on its lower side. Alternatively, the loading opening can also be arranged angularly offset on the side. In this case, the inner basket is rotated accordingly for loading. The treatment container has a spherical shape to keep the dead volume and the ratio of machine size to treatment volume as small as possible. This design allows it to install treatment machines with large treatment volume even in case of very tight spaces.

As bin for the treatment of the parts, an inner basket 4 is provided in the permanently installed treatment container 1, which inner basket 4 is connected via a horizontal shaft 6 extending through the wall of the treatment container to a drive motor 7. Due to this construction, the inner basket is rotated about a horizontal axis which ensures a gentle treatment of the parts. The inner basket 4 is equipped with a screen bottom 8 made of a fine-meshed sintered material which effects a very fine distribution of the media air, water, steam. Thus, a fluid bed is generated which is perfect for the treatment and results in a homogenous and good treatment quality. On its side opposing the screen bottom 8, the inner basket 4 is provided with an opening 5 which is equipped with a screen flap 9. The latter effects that the parts remain in the rotating inner basket during the treatment and that the unloading of the parts takes place correctly.

The drive motor 7 is a stepper motor. The latter allows a very accurate positioning in particular for the positions loading, treating and emptying. Due to the precise positioning it is prevented that parts get to the wrong places, e.g. are not completely unloaded.

Figure 2:
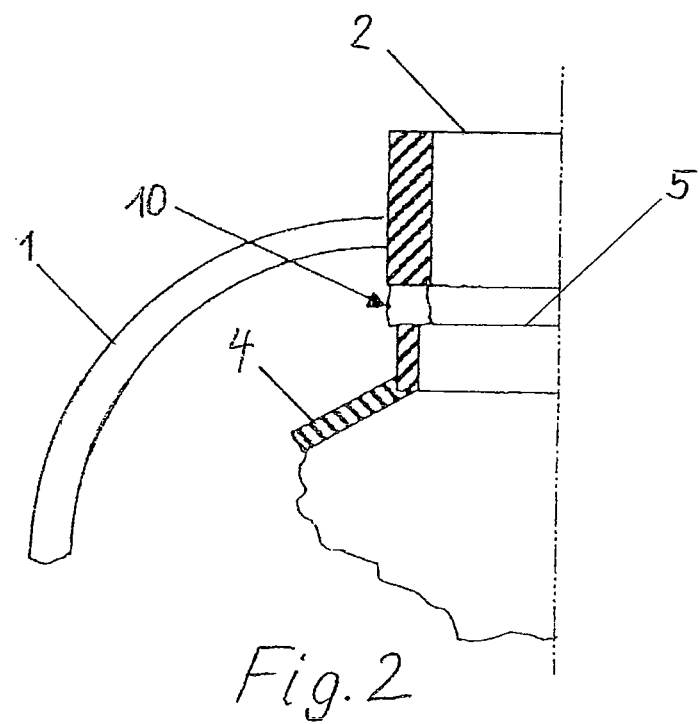
FIG. 2 shows a detail of the connection between casing and inner basket.

The treatment media air, water, steam etc. are fed through the unloading opening located on the lower side of the container and discharged through opening 2 arranged on top. In order to control the media flow correctly, a movable seal 10 is provided, as shown in FIG. 2. The seal connects the rotating inner basket 4 with the casing 1 in such a manner that no media can flow past the outside of the inner basket but all necessary media flow through the screen bottom 8 and flow through the parts in such a manner that a proper treatment is ensured.

The technical implementation is solved with an inflatable seal 10. For the present case of use, said seal can be used under sterile conditions because it functions similar to a diaphragm valve commonly used in the sterile technology.

By means of transport containers which can be built in a simple manner, a temporary storage of the parts to be treated is possible under sterile conditions.

Figure 3:
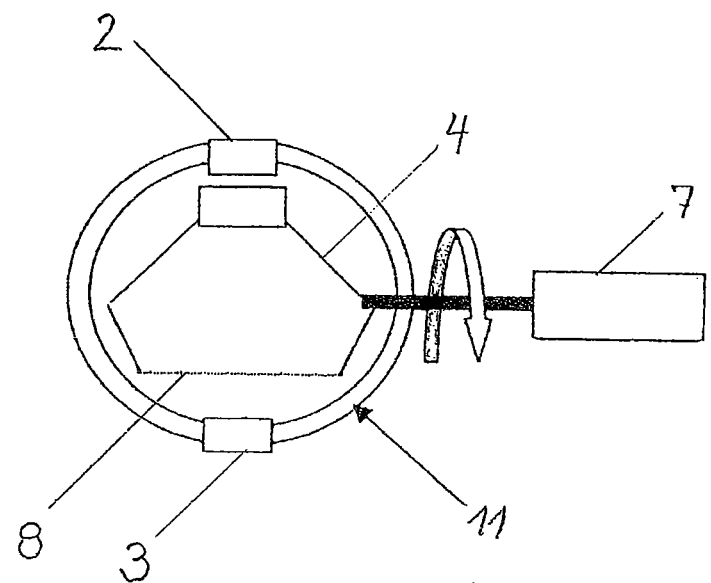
FIG. 3 shows a version of the device with cooling unit.
Figure 4:
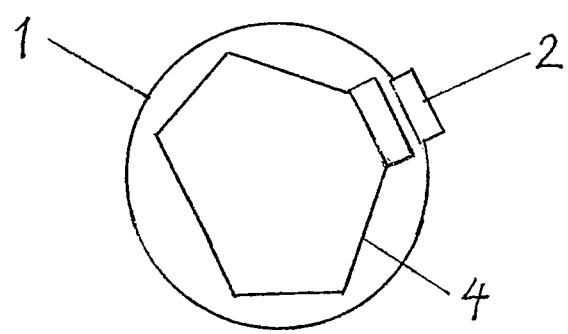
FIG. 4 shows a schematically illustrated alternative embodiment.

As shown in FIG. 3, if needed, the treatment container can be equipped with a cooling unit. This cooling unit is implemented by means of a double casing 11 or by means of a pipe coil. Cooling the parts has normally to be carried out under sterile conditions; this means that after the sterilization with steam, the parts must not come into contact again with liquid media. Therefore, cooling is carried out with a gas, e.g. air. The parts and also the treatment container have to be cooled which takes a long time with gases due to their very small heat capacity and requires high gas consumption. Cooling the treatment container by means of a cooling medium, e.g. cooling water, results in shorter cycle times for the treatment of the parts.

The invention claimed is:

1. A device for gently cleaning, sterilizing and drying large quantities of parts in a fluid bed, comprising:
   a stationary treatment container defining a casing having an interior, said treatment container having a top side and a bottom side, said treatment container having means for introducing media, and said top side of the treatment container provided with an opening for removing media from the interior of the casing and through which parts may be passed;
   an inner basket provided in said interior of said casing, said inner basket rotatable about a horizontal axis, said inner basket having a top side, an opposing bottom side, and a solid side wall connecting the top and bottom sides, said bottom side of said inner basket comprising a screen bottom through which media can flow so as to generate a fluidized bed in said inner basket, said top side of said inner basket having an opening through which parts may be passed, and
   an inflatable seal positioned between the opening on the top side of the treatment container and the opening on the top side of said rotatable inner basket, wherein, when the seal is inflated, the opening at the top side of the rotatable inner basket is open to and sealingly connected with the opening in the top side of the treatment container whereby parts can be loaded into the inner basket and media can flow through the screen bottom out through the opening in the top side of the treatment container but not flow past and around the inner basket, and when the seal is deflated the inner basket can be disconnected from the treatment container and rotated about the horizontal axis.

2. A device according to claim 1, wherein the treatment container has a spherical shape.

3. A device according to claim 1, wherein the device further comprises a stepper motor or servo motor arranged outside of said treatment container operatively connected for horizontally rotating said inner basket.

4. A device according to claim 1, wherein said opening of the inner basket is provided with a screen flap arranged opposite to the screen bottom.

5. A device according to claim 1, wherein said device further comprises a cooling unit arranged on the treatment container.

6. A device according to claim 1, wherein said parts comprise medical parts.

7. A device according to claim 6 wherein said medical parts comprise part of syringes.

8. A device according to claim 6, wherein said parts comprise ampoules.

* * * * *